US011426728B2

(12) United States Patent
Im et al.

(10) Patent No.: US 11,426,728 B2
(45) Date of Patent: Aug. 30, 2022

(54) APPARATUS FOR HIGH THROUGHPUT CONTINUOUS DROPLET ELECTROPORATION FOR DELIVERY OF A MATERIAL, AND A METHOD FOR DROPLET ELECTROPORATION USING THE SAME

(71) Applicant: PUKYONG NATIONAL UNIVERSITY INDUSTRY-UNIVERSITY COOPERATION FOUNDATION, Busan (KR)

(72) Inventors: Do Jin Im, Busan (KR); Myung Mo Ahn, Yongin-si (KR); Byeong Sun Yoo, Paju-si (KR)

(73) Assignee: PUKYONG NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 563 days.

(21) Appl. No.: 16/660,331

(22) Filed: Oct. 22, 2019

(65) Prior Publication Data

US 2020/0122138 A1 Apr. 23, 2020

(30) Foreign Application Priority Data

Oct. 22, 2018 (KR) .................. 10-2018-0126110

(51) Int. Cl.
*B01L 3/00* (2006.01)
*C12N 13/00* (2006.01)

(52) U.S. Cl.
CPC .......... *B01L 3/50273* (2013.01); *C12N 13/00* (2013.01); *B01L 2200/06* (2013.01);
(Continued)

(58) Field of Classification Search
CPC ......... B01L 2200/06; B01L 2200/0673; B01L 2300/047; B01L 2300/0645;
(Continued)

(56) References Cited

U.S. PATENT DOCUMENTS

| 2016/0053283 | A1* | 2/2016 | Wang | C12N 9/1205 |
| | | | | 435/461 |
| 2016/0333302 | A1* | 11/2016 | Im | C12N 15/8206 |
| 2017/0003310 | A1* | 1/2017 | Shohmi | G01N 35/00584 |

FOREIGN PATENT DOCUMENTS

| KR | 10-2009-0018469 | 2/2009 |
| KR | 10-1598847 | 3/2016 |

(Continued)

*Primary Examiner* — Jennifer Wecker
*Assistant Examiner* — Jonathan Bortoli
(74) *Attorney, Agent, or Firm* — Norton Rose Fulbright US LLP

(57) ABSTRACT

An electroporation device is disclosed, which includes a first tubular electrode including a first inlet and a first outlet; an aqueous solution supply connected to the first tubular electrode and configured for supplying an aqueous solution to the first tubular electrode and for allowing a droplet of the aqueous solution to be discharged from the first outlet of the first tubular electrode, the aqueous solution contains a cell and a delivery target substance; a second tubular electrode including a second inlet and a second outlet, wherein the second inlet is spaced away from the first outlet at a spacing corresponding to a size of a portion of the droplet; a power supply for applying a voltage to the electrodes for electroporation of the cell in the droplet; and a droplet sucking unit connected to the second electrode and configured for allowing the droplet to be sucked into the second electrode.

15 Claims, 4 Drawing Sheets

(52) U.S. Cl.
CPC . *B01L 2300/047* (2013.01); *B01L 2300/0645* (2013.01); *B01L 2300/165* (2013.01); *B01L 2400/049* (2013.01)

(58) Field of Classification Search
CPC ....... B01L 2300/0832; B01L 2300/165; B01L 2400/049; B01L 3/50273; B01L 3/502784; C12N 13/00; C12N 15/87
See application file for complete search history.

(56) References Cited

FOREIGN PATENT DOCUMENTS

| | | |
|---|---|---|
| KR | 10-2016-0079659 | 7/2016 |
| KR | 10-2018-0126110 | 11/2018 |

\* cited by examiner

APPARATUS FOR HIGH THROUGHPUT CONTINUOUS DROPLET ELECTROPORATION FOR DELIVERY OF A MATERIAL, AND A METHOD FOR DROPLET ELECTROPORATION USING THE SAME

CROSS REFERENCE TO RELATED APPLICATIONS

The present application claims priority to and the benefit of Korean Patent Application No. 10-2018-0126110, filed Oct. 22, 2018.

BACKGROUND

1. Field

The present disclosure relates to a droplet-based electroporation device, and more particularly, to a continuous droplet-based electroporation device.

2. Description of Related Art

Delivering an external genetic substance to a cell to express a desired trait or create a new cell is a core technology of genetic engineering. A method of delivering the substance to the cell is divided into two ways: using a virus and not using a virus.

The use of the viruse has an advantage of being able to deliver the substance effectively to the cell. However, there are a risk and side effect that the virus infection may occur in vivo, and there is a difficulty in designing the virus suitable for each cell type.

One of the methods that does not use the virus is an electroporation method that delivers a substance by temporarily applying a high voltage electric pulse to temporarily increase permeability of a cell membrane. The electroporation method may be applied regardless of the cell type and may have a relatively high transfer efficiency of the external substance. Thus, the electroporation method together with a chemical method among the non-virus based methods is most widely used.

A currently commercially available electroporation device has a disadvantage of very low cell viability because the device uses the high voltage.

Further, the commercially available electroporation device may cause cell contamination during electroporation, may require an expensive power supply capable of maintaining a current of several amperes at a high voltage. A replaced component thereof is expensive.

Further, the commercially available electroporation device has a disadvantage that a variation of an experimental result is relatively large because the electroporation device is relatively large.

In order to overcome the above disadvantages of the commercially available electroporation device, the electroporation device using microfluidic technology has been developed. The electroporation device using microfluidic technology has a small size and thus achieve the same electroporation effect at a low voltage level and use a small amount of a sample and realize a high cell viability. However, the current electroporation device using the microfluidic technology uses a small amount of cells, the number of cells that may be obtained at a time is small. The device is composed of a micro element and thus a disadvantage in that user convenience is poor.

Korean Patent Application No. 2009-0018469 discloses a device for analyzing the electroporation effect of a cell using a microelement and a method for analyzing the electroporation effect of a cell using the same. However, the electroporation device as proposed in this patent document has poor user convenience because the cell is perforated in a microchannel formed on a substrate.

Further, since the number of cells that may be contained in the fluid introduced into a flow path of the microelement is extremely small, the electroporation device as proposed in this patent document may not have a biotechnological application involving transferring a substance into cells and culturing the cells to which the substance has been delivered.

Korean Patent No. 10-1598847 discloses a droplet-mediated electroporation device to overcome the above disadvantage. However, the electroporation method as proposed in this patent document has a disadvantage that a user must manually supply individual droplets using pipette or the like. Thus, the number of cells as treated within a limited time may be small. Thus, the prior art device is very disadvantageous in terms of productivity.

Therefore, there is a need to develop a new electroporation device that may overcome the disadvantage of the low productivity while maintaining high cell viability and substance transfer efficiency as the advantages of the electroporation device using the droplets.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose of the present disclosure is to provide a continuous droplet-based electroporation device that may achieve very high electroporation productivity together with high cell viability and high external substance transfer efficiency.

Another purpose of the present disclosure is to provide a continuous droplet-based electroporation device which may continuously maintain supply of droplets and collection of the droplets after electroporation, such that the electroporation may be continuously performed for a desired time duration without interruption, and thus may be useful when electroporation of many cells for a limited short time is required.

Purposes of the present disclosure are not limited to the above-mentioned purpose. Other purposes and advantages of the present disclosure as not mentioned above may be understood from following descriptions and more clearly understood from embodiments of the present disclosure. Further, it will be readily appreciated that the purposes and advantages of the present disclosure may be realized by features and combinations thereof as disclosed in the claims.

A first aspect of the present disclosure provides a continuous droplet-based electroporation device comprising: a first tubular electrode constructed in a hollow cylindrical shape and including a first inlet and a first outlet; an aqueous solution supply connected to the first tubular electrode and configured for supplying an aqueous solution to the first tubular electrode and for allowing a droplet of the aqueous solution to be discharged from the first outlet of the first tubular electrode, wherein the aqueous solution contains a cell and a delivery target substance; a second tubular electrode constructed in a hollow cylindrical shape and including a second inlet and a second outlet, wherein the second tubular electrode is oriented to be coaxial with the first tubular electrode, wherein the second inlet is spaced away from the first outlet at a spacing corresponding to a size of a portion of the droplet; a power supply for applying a voltage to the first tubular electrode and the second tubular electrode for electroporation of the cell in the droplet; and a droplet sucking unit connected to the second tubular electrode and configured for allowing the droplet to be sucked into the second tubular electrode immediately after the electroporation.

In one implementation of the first aspect, the continuous droplet-based electroporation device further comprises an oil storage including a container containing therein oil, wherein the first outlet of the first tubular electrode and the second inlet of the second tubular electrode are received in the container and are spaced away from each other.

In one implementation of the first aspect, the oil is electrically non-conductive.

In one implementation of the first aspect, the aqueous solution supply is configured to generate a supply pressure to gradually increase a size of the droplet at the first outlet so that a portion of the droplet contacts the second inlet, wherein the droplet sucking unit is configured to generate a sucking pressure to allow the droplet to be sucked into the second inlet when the droplet is in contact with the second inlet.

In one implementation of the first aspect, each of the first tubular electrode and the second tubular electrode is oriented in a parallel manner to a gravity direction, wherein the supply direction of the aqueous solution and the sucking direction of the droplet are opposite to the gravity direction.

In one implementation of the first aspect, each of the first tubular electrode and the second tubular electrode includes a hydrophobic coating layer coated on each of an inner face and an outer face thereof.

In one implementation of the first aspect, the hydrophobic coating layer is electrically conductive.

In one implementation of the first aspect, the first tubular electrode and the second tubular electrode are configured to be movable so that the spacing between the first outlet and the second inlet is adjusted.

In one implementation of the first aspect, the droplet-based electroporation device further comprises an oil supply connected to the oil storage and supplying the non-conductive oil into the container of the oil storage.

In one implementation of the first aspect, the oil is sucked toward the droplet sucking unit during forming and sucking the droplet, wherein the droplet-based electroporation device further comprises an oil collector installed on an oil sucking path, wherein the oil collector is configured for separating the oil from the aqueous solution and collecting the separated oil during sucking the droplet.

In one implementation of the first aspect, the power supply is configured to adjust a magnitude and an application time duration of the voltage.

In one implementation of the first aspect, the first tubular electrode includes a plurality of first tubular electrodes, and the second tubular electrode includes a plurality of second tubular electrodes, wherein a plurality of series combinations between the first tubular electrodes and second tubular electrodes are arranged in a parallel manner.

A second aspect of the present disclosure provides a continuous droplet-based electroporation method using the droplet-based electroporation device as defined above, the method comprising: supplying an aqueous solution containing a cell and a delivery target substance in a direction opposite to a gravity direction and discharging a droplet of the aqueous solution; applying a voltage to the droplet to perform electroporation of the cell; and sucking the droplet in a direction opposite to a gravity direction at the same time as the electroporation of the cell.

Effects of the present disclosure are as follows but are not limited thereto.

In accordance with the present disclosure, the continuous droplet-based electroporation device may achieve very high electroporation productivity together with high cell viability and high external substance transfer efficiency.

Further, the continuous droplet-based electroporation device may continuously maintain supply of droplets and collection of the droplets after electroporation, such that the electroporation may be continuously performed for a desired time duration without interruption, and thus may be useful when electroporation of many cells for a limited short time is required.

Further, the use of the non-conductive oil may block the external contaminant source that may be introduced during many experiments.

Further, conducting dozens of hundreds of droplet-based electroporation experiments for a small time duration in a consistent manner may reduce the experimental deviation of the electroporation experiment results.

In addition to the effects as described above, specific effects of the present disclosure are described together with specific details for carrying out the invention.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTIONS

Figure 1:
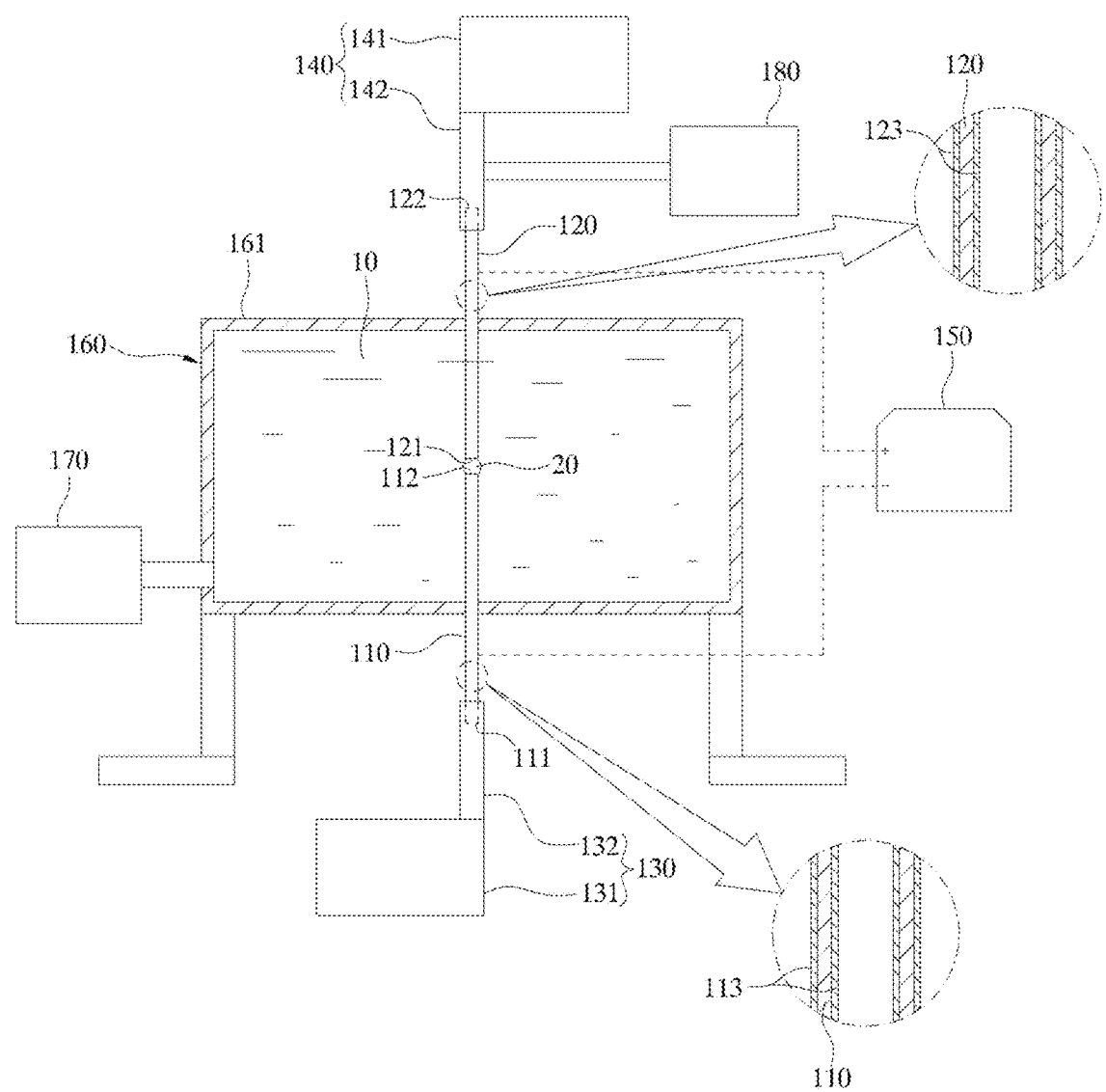
FIG. 1 is a view for illustrating a continuous droplet-based electroporation device according to an embodiment of the present disclosure.

For simplicity and clarity of illustration, elements in the figures are not necessarily drawn to scale. The same reference numbers in different figures denote the same or similar elements, and as such perform similar functionality. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" or "beneath" a second element or layer, the first element may be disposed directly on or beneath the second element or may be disposed indirectly on or beneath the second element with a third element or layer being disposed between the first and second elements or layers. It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a view for illustrating a continuous droplet-based electroporation device according to an embodiment of the present disclosure.

Referring to FIG. 1, a droplet-based electroporation device according to an embodiment of the present disclosure may include a first tubular electrode 110, an aqueous solution supply 130, a second tubular electrode 120, a droplet sucking unit 140, a power supply 150, and an oil storage 160.

The first tubular electrode 110 may be embodied in a form of a hollow cylinder, and include a first inlet 111 at one end thereof and a first outlet 112 opposite to the first inlet 111. The first inlet 111 refers to an inlet into which an aqueous solution including a cell and a delivery target substance is introduced. The first outlet 112 means an outlet through which the introduced aqueous solution is discharged in form of a droplet. In one example, the first tubular electrode 110 may have a cylindrical shape.

The aqueous solution supply 130 may be connected to the first tubular electrode 110 to supply the aqueous solution containing the cells and the delivery target substance to the inlet of the first tubular electrode 110 such that the solution is discharged in a form of the droplet from the first outlet of the first tubular electrode. In this connection, the aqueous solution supply 130 has a supply pressure that can gradually increase a size of the droplet in the first outlet so that a portion of the droplet may contact the second inlet. In one example, the aqueous solution supply 130 may include a first pump 131a and a first pump connection pipe 132 connecting the first pump 131 to the first tubular electrode 110. The first pump 131 may be embodied to have a piston capable of pumping the aqueous solution. The first pump connection pipe 132 may be made of an insulating material.

The second tubular electrode 120 may be embodied in a form of a hollow cylinder, and include a second inlet 121 at one end thereof and a second outlet 122 opposite to the second inlet 121. The second tubular electrode 120 is coaxial with the first tubular electrode 110. In this connection, the second inlet 121 of the second tubular electrode 120 may face away the first outlet 112 of the first tubular electrode 110 in a predetermined spacing. The spacing between the first outlet 112 and the second inlet 121 may be sized such that a portion of the droplet can contact the second inlet 121. The second inlet 121 means an inlet into which the droplet is sucked, and the second outlet 122 means an outlet through which the sucked droplet is discharged.

The droplet sucking unit 140 is connected to the second tubular electrode 120. When the droplet contacts the second inlet 121, the droplet sucking unit 140 may generate a suction pressure capable of sucking the droplet to allow the droplet to be sucked into the second tubular electrode 120. In one example, the droplet sucking unit 140 may include a second pump 141 and a second pump connection pipe 142 connecting the second pump 141 to the second tubular electrode 120. The second pump 141 may be embodied in a form including a piston capable of pumping an aqueous solution. The second pump connection pipe 142 may made of be an insulating material.

In this connection, the first tubular electrode 110 and the second tubular electrode 120 may be configured to be movable so that a distance between the first outlet 112 and the second inlet 121 is adjusted. There is no particular limitation on a configuration for controlling the distance between the first outlet 112 and the second inlet 121. The configuration for controlling the distance between the first outlet 112 and the second inlet 121 may include any mechanical device capable of physically moving the first tubular electrode 110 and the second tubular electrode 120.

Further, each of the first tubular electrode 110 and the second tubular electrode 120 may be oriented a parallel manner to the gravity direction. In this connection, the supply direction of the aqueous solution and the suction direction of the droplet may be the reverse direction to the gravity direction. That is, bubbles may be generated in a process of supplying the aqueous solution to generate the droplet and of performing electroporation of the cell in the droplet. In this connection, bubbles having a lower density than the aqueous solutions have tendency to rise up. Thus, when the direction of supply of the aqueous solution is opposite to the gravity direction, the directions of movements of the bubbles and the aqueous solution are the same. Accordingly, the bubbles may be easily discharged without resistance due to the aqueous solution, and thus the generation of the droplets may be facilitated.

Further, each of the first tubular electrode 110 and the second tubular electrode 120 may include each of hydrophobic coating layers 113 and 123 coated on both of inner and outer faces thereof. Each of the hydrophobic coating layers 113 and 123 may be electrically conductive so that current may flow therein during the electroporation process. The hydrophobic coating layers 113 and 123 may prevent the aqueous solution and droplet from sticking to the inner and outer faces of the tube.

The power supply 150 applies a voltage to the first tubular electrode 110 and the second tubular electrode 120. To this end, the power supply 150 may be connected to the first tubular electrode 110 and the second tubular electrode 120. In one example, a negative (−) voltage may be applied to the first tubular electrode 110, while a positive (+) voltage may be applied to the second tubular electrode 120. However, the present disclosure may not be limited thereto. The power supply 150 may be configured to adjust a magnitude of the voltage and the application time duration.

The oil storage 160 may have a configuration in which an non-conductive oil 10 is stored in a container 161. The first outlet 112 of the first tubular electrode 110 and the first inlet 111 of the second tubular electrode 120 may be inserted into the container 161 of the oil storage 160 and may face away with each other therein. Therefore, the formation of the droplets and the suction of the droplets may proceed inside the oil 10. The oil 10 is preferably low in viscosity so that the movement of the droplets is easy. Since the oil 10 is non-conductive, the droplet 20 is electrically insulated from surroundings when the cell in the droplet 20 is electroporated.

Figure 2:
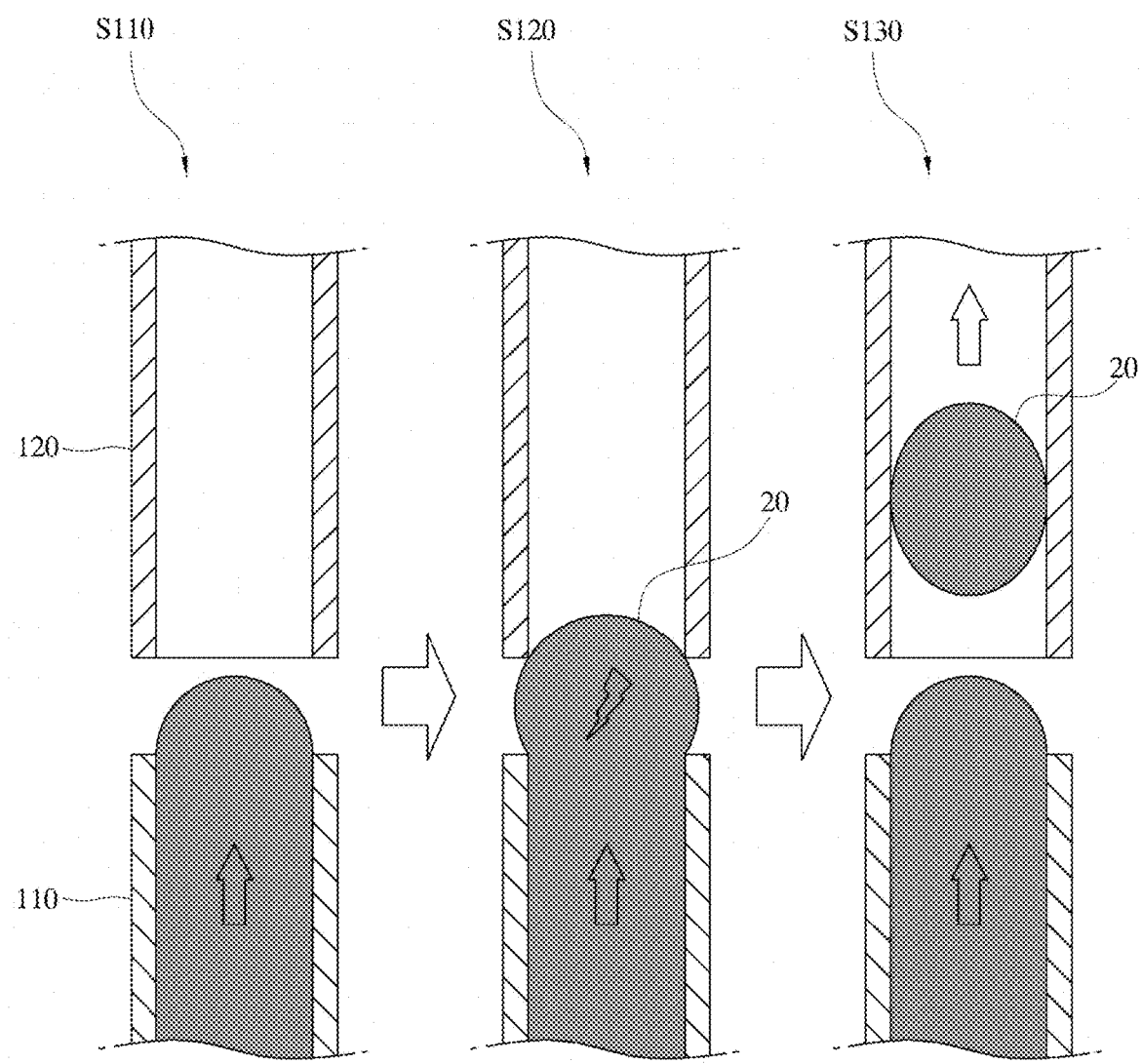
FIG. 2 is a view illustrating droplet generation, droplet movement, and droplet-based electroporation in a droplet-based electroporation method using a continuous droplet-based electroporation device according to an embodiment of the present disclosure.

Hereinafter, the droplet generation and suction process using the droplet-based electroporation device according to an embodiment of the present disclosure will be described. FIG. 2 is a view illustrating droplet generation, droplet movement, and droplet-based electroporation in a droplet-based electroporation method using a continuous droplet-based electroporation device according to an embodiment of the present disclosure.

Referring to FIG. 2, a droplet-based electroporation method using a droplet-based electroporation device according to an embodiment of the present disclosure may include supplying an aqueous solution containing a cell and a delivery target substance in a reverse direction to a gravity direction and discharging a droplet of the aqueous solution (S110); by applying a voltage to the droplet to perform electroporation of the cell in the droplet (S120); and suctioning the droplet in the reverse direction to the gravity direction at the same time as the electroporation of the cell. A following description describes the steps in detail.

First, the aqueous solution supply 130 supplies an aqueous solution containing a cell and a delivery target substance to the inside of the first tubular electrode 110. Then, the power 150 supply may apply a voltage to the first tubular electrode 110 and the second tubular electrode 120, and then, the droplet sucking unit 140 may be turned on.

The aqueous solution supplied to the inside of the first tubular electrode 110 may gradually turn into a droplet form at the first outlet 112 of the first tubular electrode 110 as the aqueous solution gradually fills the inside of the first tubular electrode 110. In this process, the oil in the oil storage 160 may be first sucked through the second inlet 121 of the second tubular electrode 120 by the droplet sucking unit 140.

When the droplet 20 gradually increases in size to become in contact with the second inlet 121 of the second tubular electrode 120, the voltage applied to the first tubular electrode 110 and the second tubular electrode 120 may be transferred to the droplet 20. Thus, the electroporation is performed to the cells in the droplet 20. At this time, the delivery target substance may be introduced into the cells.

Simultaneously with the electroporation, the droplet 20 and oil 10 may be sucked into the second tubular electrode 120 from the second inlet 121 of the second tubular electrode 120 using the droplet sucking unit 140.

This process may repeat continuously. That is, after the droplet 20 which has undergone the electroporation is sucked into the second tubular electrode 120, the process of generating a new droplet may be repeated. In this way, the electroporation may proceed continuously.

Figure 3:
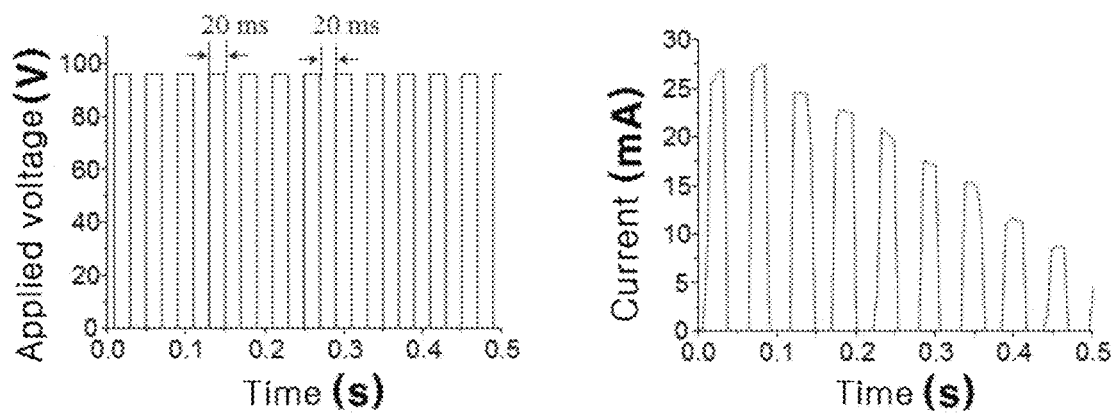
FIG. 3 illustrates a change in a voltage and current distribution over time as obtained by performing electroporation using a droplet-based electroporation device according to an embodiment of the present disclosure.

FIG. 3 illustrates a change in a voltage and current distribution over time obtained by performing electroporation using a droplet-based electroporation device according to an embodiment of the present disclosure.

In an embodiment, the voltage 96V may be applied to the second tubular electrode 120 in a form of a pulse (the voltage application is activated for 20 ms and then is deactivated for 20 ms and the application/non-application are repeated), while the first electrode may be connected to a ground. As the electroporation was applied to the droplets, the change of current flow was detected. After the initial current flow of about 27 mA, the current value was gradually decreased. This may be understood to be due to a fact that the size of the droplet 20 decreases as the droplet 20 is sucked toward the second tubular electrode 120 such that a total resistance increases over time. In addition, This may be further due to the effect of increasing the resistance, as caused by bubbles generated during the electroporation process.

As shown in FIG. 3, a phenomenon in which a strong current flows initially and then the current gradually decreases may be due to the fact that in the electroporation process, a high current is initially used to form holes in the cell membrane, and, then, a relatively low current is used to deliver the substance through the holes formed in the cell membrane into the cell. Thus, a positive effect that the electroporation may be performed with minimal damage to the cells may be achieved.

Figure 4:
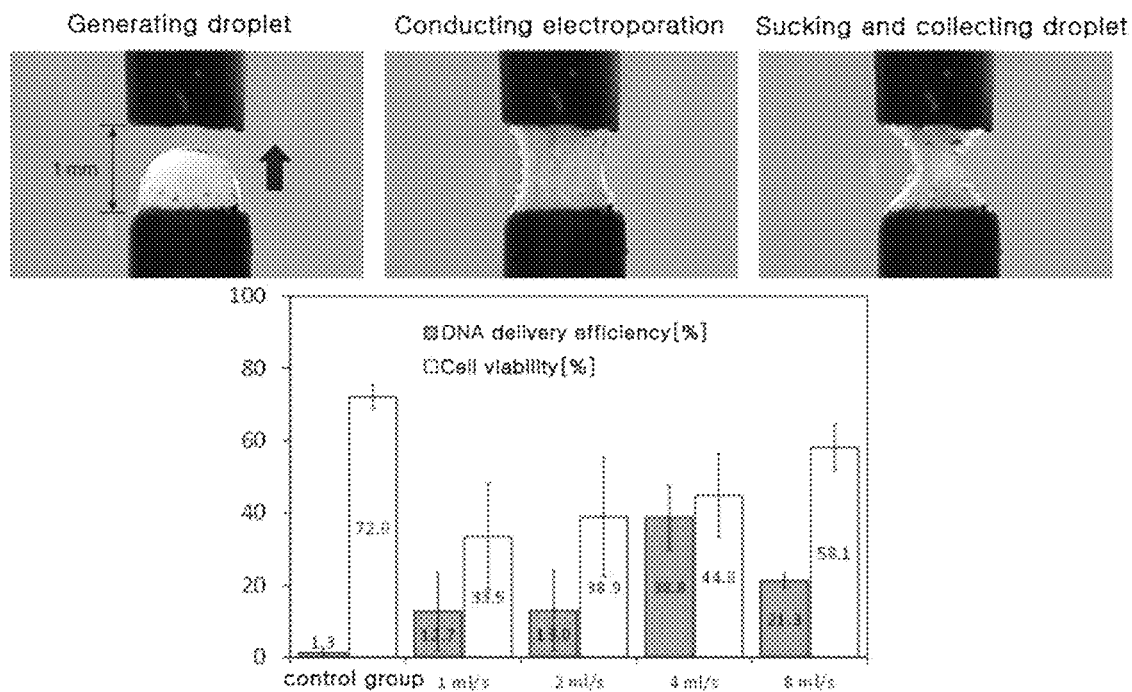
FIG. 4 is a view showing a state in which plasmid DNA for synthesizing a fluorescent protein is delivered to microalgae cells using a droplet-based electroporation device according to an embodiment of the present disclosure and is then expressed therein, and showing an experiment result.

FIG. 4 is a view showing a state in which plasmid DNA for synthesizing a fluorescent protein is delivered to microalgae cells using a droplet-based electroporation device according to an embodiment of the present disclosure and is then expressed therein, and showing an experiment result.

In FIG. 4, an upper image shows a process of generating droplets and conducting electroporation and sucking and collecting droplets after the electroporation. The lower graph shows the DNA delivery efficiency and cell viability data based on the droplet flow rate changes when applying the voltage 192V. In this connection, the flow rate of the collected non-conductive oil and droplet was four times the feed flow rate of the aqueous solution.

Referring to FIG. 4, as the flow rate increases, the application time duration of the voltage applied during the electroporation decreases to increase the cell viability, while the substance delivery efficiency shows the maximum level at an appropriate flow rate.

In accordance with the present disclosure, the continuous droplet-based electroporation device may achieve very high electroporation productivity together with high cell viability and high external substance transfer efficiency.

Further, the continuous droplet-based electroporation device may continuously maintain supply of droplets and collection of the droplets after electroporation, such that the electroporation may be continuously performed for a desired time duration without interruption, and thus may be useful when electroporation of many cells for a limited short time is required.

Further, the use of the non-conductive oil may block the external contaminant source that may be introduced during many experiments.

Further, conducting dozens of hundreds of droplet-based electroporation experiments for a small time duration in a consistent manner may reduce the experimental deviation of the electroporation experiment results.

In one embodiment of the present disclosure, the droplet-based electroporation device may further include an oil supply 170 and an oil collector 180.

The oil supply 170 may be connected to the oil storage 160 and may be configured to supply the non-conductive oil into the container 161 of the oil storage 160. The oil supply 170 may be embodied in a form of a pump for supplying the non-conductive oil to the oil storage 160 by pumping the oil from an oil reservoir. The oil supply 170 may be used for oil replenishment as the oil is sucked into the second electrode together with the droplet as the droplet is sucked into the second electrode.

The oil collector 180 may be installed on a path along which the oil is sucked, and may be configured to separate the oil from the aqueous solution in the process of sucking the droplets and to collect the separated oil. A configuration of the oil collector 180 is not particularly limited. For example, the oil collector 180 may be configured to separate the oil from the aqueous solution using a difference in density between the oil and the aqueous solution on the path along which oil is suctioned, that is, on the second pump connection pipe 142. The oil collector 180 may be configured to collect the used oil and supply the collected oil to the oil storage 160 again, thereby enabling reuse of the oil.

Figure 5:
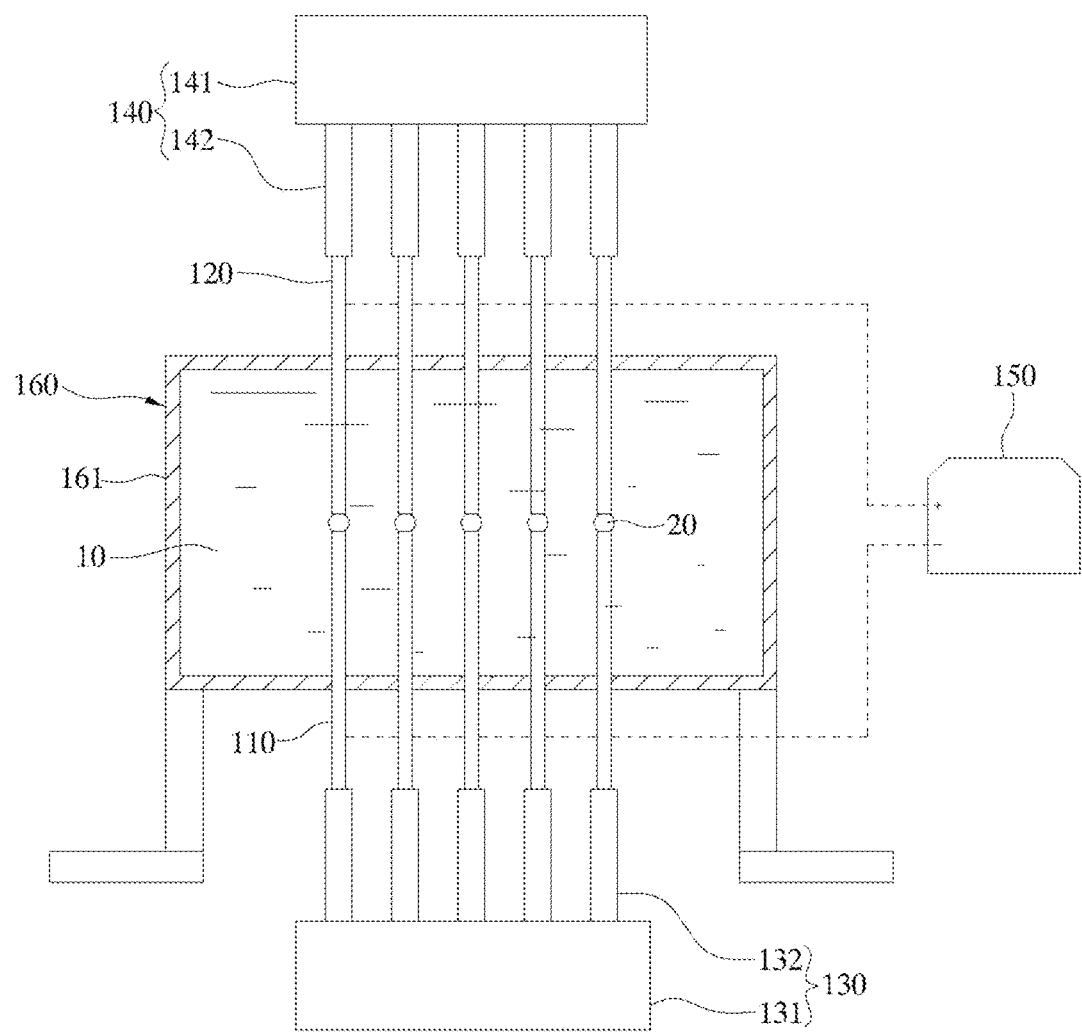
FIG. 5 illustrates a state in which a plurality of series combinations of first tubular electrodes and second tubular electrodes are arranged in a parallel manner in a continuous droplet-based electroporation device according to an embodiment of the present disclosure.

FIG. 5 illustrates a state in which a plurality of series combinations of first tubular electrodes and second tubular electrodes are arranged in a parallel manner in a continuous droplet-based electroporation device according to an embodiment of the present disclosure.

Referring to FIG. 5, in the droplet-based electroporation device according to an embodiment of the present disclosure, a plurality of series combinations of first tubular electrodes 110 and second tubular electrodes 120 are arranged in a parallel manner. In this case, the electroporation productivity may be further increased.

As described above, the present disclosure is described with reference to the drawings. However, the present disclosure is not limited by the embodiments and drawings disclosed in the present specification. It will be apparent that various modifications may be made thereto by those skilled in the art within the scope of the present disclosure. Furthermore, although the effect resulting from the features of the present disclosure has not been explicitly described in the description of the embodiments of the present disclosure, it is obvious that a predictable effect resulting from the features of the present disclosure should be recognized.

What is claimed is:

1. A continuous droplet-based electroporation device comprising:
    a first tubular electrode constructed in a hollow cylindrical shape and including a first inlet and a first outlet;
    an aqueous solution supply connected to the first tubular electrode and configured for supplying an aqueous solution to the first tubular electrode and for allowing a droplet of the aqueous solution to be discharged from the first outlet of the first tubular electrode, wherein the aqueous solution contains a cell and a delivery target substance;
    a second tubular electrode constructed in a hollow cylindrical shape and including a second inlet and a second outlet, wherein the second tubular electrode is oriented to be coaxial with the first tubular electrode, wherein the second inlet is spaced away from the first outlet at a spacing corresponding to a size of a portion of the droplet;
    a power supply for applying a voltage to the first tubular electrode and the second tubular electrode for electroporation of the cell in the droplet; and
    a droplet sucking unit connected to the second tubular electrode and configured for allowing the droplet to be sucked into the second tubular electrode immediately after the electroporation.

2. The continuous droplet-based electroporation device of claim 1, wherein the continuous droplet-based electroporation device further comprises an oil storage including a container containing therein oil,
    wherein the first outlet of the first tubular electrode and the second inlet of the second tubular electrode are received in the container and are spaced away from each other.

3. The continuous droplet-based electroporation device of claim 2, wherein the oil is electrically non-conductive.

4. The continuous droplet-based electroporation device of claim 1, wherein the aqueous solution supply is configured to generate a supply pressure to gradually increase a size of the droplet at the first outlet so that a portion of the droplet contacts the second inlet,
    wherein the droplet sucking unit is configured to generate a sucking pressure to allow the droplet to be sucked into the second inlet when the droplet is in contact with the second inlet.

5. The continuous droplet-based electroporation device of claim 2, wherein the aqueous solution supply is configured to generate a supply pressure to gradually increase a size of the droplet at the first outlet so that a portion of the droplet contacts the second inlet,
    wherein the droplet sucking unit is configured to generate a sucking pressure to allow the droplet to be sucked into the second inlet when the droplet is in contact with the second inlet.

6. The continuous droplet-based electroporation device of claim 1, wherein each of the first tubular electrode and the second tubular electrode is oriented in a parallel manner to a gravity direction, wherein the supply direction of the aqueous solution and the sucking direction of the droplet are opposite to the gravity direction.

7. The continuous droplet-based electroporation device of claim 2, wherein each of the first tubular electrode and the second tubular electrode is oriented in a parallel manner to a gravity direction, wherein the supply direction of the aqueous solution and the sucking direction of the droplet are opposite to the gravity direction.

8. The continuous droplet-based electroporation device of claim 1, wherein each of the first tubular electrode and the second tubular electrode includes a hydrophobic coating layer coated on each of an inner face and an outer face thereof.

9. The continuous droplet-based electroporation device of claim 8, wherein the hydrophobic coating layer is electrically conductive.

10. The continuous droplet-based electroporation device of claim 1, wherein the first tubular electrode and the second tubular electrode are configured to be movable so that the spacing between the first outlet and the second inlet is adjusted.

11. The continuous droplet-based electroporation device of claim 2, wherein the droplet-based electroporation device further comprises an oil supply connected to the oil storage and supplying the non-conductive oil into the container of the oil storage.

12. The continuous droplet-based electroporation device of claim 2, wherein the oil is sucked toward the droplet sucking unit during forming and sucking the droplet, wherein the droplet-based electroporation device further comprises an oil collector installed on an oil sucking path, wherein the oil collector is configured for separating the oil from the aqueous solution and collecting the separated oil during sucking the droplet.

13. The continuous droplet-based electroporation device of claim 1, wherein the power supply is configured to adjust a magnitude and an application time duration of the voltage.

14. The continuous droplet-based electroporation device of claim 1, wherein the first tubular electrode includes a plurality of first tubular electrodes, and the second tubular electrode includes a plurality of second tubular electrodes, wherein a plurality of series combinations between the first tubular electrodes and second tubular electrodes are arranged in a parallel manner.

15. A continuous droplet-based electroporation method using the droplet-based electroporation device of claim 1, the method comprising:

supplying an aqueous solution containing a cell and a delivery target substance in a direction opposite to a gravity direction and discharging a droplet of the aqueous solution;

applying a voltage to the droplet to perform electroporation of the cell; and sucking the droplet in a direction opposite to a gravity direction at the same time as the electroporation of the cell.

* * * * *